(12) United States Patent
Kincaid et al.

(10) Patent No.: US 10,099,961 B2
(45) Date of Patent: Oct. 16, 2018

(54) FLUORESCENT BUILDING PRODUCT AND RELATED DETECTION METHOD

(71) Applicant: United States Gypsum Company, Chicago, IL (US)

(72) Inventors: Tyler Kincaid, Beach Park, IL (US); Charles J. Miller, Johnsburg, IL (US)

(73) Assignee: UNITED STATES GYPSUM COMPANY, Chicago, IL (US)

( * ) Notice: Subject to any disclaimer, the term of this patent is extended or adjusted under 35 U.S.C. 154(b) by 0 days.

(21) Appl. No.: 14/824,780

(22) Filed: Aug. 12, 2015

(65) Prior Publication Data

US 2017/0044062 A1 Feb. 16, 2017

(51) Int. Cl.
| | |
|---|---|
| *C04B 16/00* | (2006.01) |
| *C04B 28/00* | (2006.01) |
| *C04B 26/06* | (2006.01) |
| *C04B 28/14* | (2006.01) |
| *E04F 21/02* | (2006.01) |
| *G01N 21/63* | (2006.01) |
| *G01N 21/64* | (2006.01) |
| *G01N 33/38* | (2006.01) |
| *C04B 14/10* | (2006.01) |
| *C04B 14/18* | (2006.01) |
| *C04B 111/00* | (2006.01) |
| *C04B 111/80* | (2006.01) |

(52) U.S. Cl.
CPC .............. *C04B 16/00* (2013.01); *C04B 26/06* (2013.01); *C04B 28/00* (2013.01); *C04B 28/14* (2013.01); *E04F 21/026* (2013.01); *G01N 21/64* (2013.01); *G01N 21/643* (2013.01); *G01N 21/6447* (2013.01); *G01N 33/383* (2013.01); *C04B 14/10* (2013.01); *C04B 14/185* (2013.01); *C04B 2111/00672* (2013.01); *C04B 2111/807* (2013.01); *Y10T 436/13* (2015.01)

(58) Field of Classification Search
CPC ......... C04B 28/14; C04B 14/10; C04B 14/18; C04B 2103/54; C04B 2111/00672; C04B 40/0096; C04B 28/00; C04B 14/185; C04B 2103/44; C04B 2111/807; C04B 26/06; C04B 16/00; C04B 24/20; G01N 2030/8859; G01N 21/77; G01N 37/00; G01N 21/64; G01N 21/643; G01N 21/6447; G01N 33/383; Y10T 436/13; E04F 21/026
USPC .............. 436/8, 56, 164, 166, 172; 422/400, 422/82.05, 82.08; 52/232; 106/772; 250/302, 372
See application file for complete search history.

(56) References Cited

U.S. PATENT DOCUMENTS

| | | | |
|---|---|---|---|
| 2,088,412 A | | 7/1937 | Grosvenor |
| 3,930,063 A | | 12/1975 | Miller et al. |
| 3,964,294 A | | 6/1976 | Shair et al. |
| 4,131,064 A | | 12/1978 | Ryan et al. |
| 4,652,395 A | * | 3/1987 | Marcina ................... C08J 3/226 250/302 |
| 5,324,356 A | * | 6/1994 | Goodwin ............ C04B 40/0096 106/638 |
| 5,667,764 A | | 9/1997 | Kopia et al. |
| 5,747,126 A | * | 5/1998 | Van Erden ........... B65D 33/255 24/585.12 |
| 5,849,218 A | * | 12/1998 | Johansen, Jr. ...... C04B 41/5079 106/712 |
| 6,806,478 B1 | | 10/2004 | Hatfield |
| 7,485,177 B1 | * | 2/2009 | McConnell ............. C23F 11/00 106/14.05 |
| 8,642,346 B2 | * | 2/2014 | Immordino, Jr. ... C04B 40/0096 106/35 |
| 2002/0076550 A1 | | 6/2002 | Kohla et al. |
| 2003/0051638 A1 | | 3/2003 | Pomeroy |
| 2004/0098891 A1 | | 5/2004 | Hunt et al. |
| 2008/0315163 A1 | * | 12/2008 | Schroer ................... G01K 11/12 252/586 |
| 2010/0046968 A1 | * | 2/2010 | Hamby ................ G03G 15/553 399/33 |
| 2010/0222917 A1 | * | 9/2010 | Bohlig .................... B07C 5/342 700/224 |
| 2012/0082839 A1 | | 4/2012 | Ha et al. |
| 2013/0035422 A1 | * | 2/2013 | Freund ................ C04B 40/0039 524/2 |
| 2013/0145827 A1 | | 6/2013 | Walloch et al. |
| 2015/0159082 A1 | | 6/2015 | Lee et al. |

FOREIGN PATENT DOCUMENTS

| | | |
|---|---|---|
| AU | 2007200986 A1 | 9/2007 |
| JP | 2009235778 A | 10/2009 |
| PL | 399384 A1 | 12/2013 |

OTHER PUBLICATIONS

Ram et al. Abstract from Cereal Chemistry, vol. 79 (6), 2002, pp. 857-860.*
International Search Report from International Patent Application No. PCT/US2016/045542, dated Nov. 4, 2016.
Written Opinion from International Patent Application No. PCT/US2016/045542, dated Nov. 4, 2016.

* cited by examiner

*Primary Examiner* — Maureen Wallenhorst
(74) *Attorney, Agent, or Firm* — Greer, Burns & Crain, Ltd.; Pradip Sahu; Philip T. Petti

(57) ABSTRACT

A method of making an identifiable gypsum-based building product, includes incorporating a suitable amount of an optically identifiable marker into the product to be sensed by a conventional detecting device; applying the product with the marker in a conventional manner in the course of building construction, creating a finished building product; and analyzing the finished building product and optically detecting the presence of the marker in real time onsite.

9 Claims, 4 Drawing Sheets
(1 of 4 Drawing Sheet(s) Filed in Color)

FLUORESCENT BUILDING PRODUCT AND RELATED DETECTION METHOD

BACKGROUND

The present invention relates generally to construction or remodeling materials that are identifiable through analysis of a tagging material, and more particularly to such materials that are produced or formulated using settable, water-based slurries.

In the construction of buildings, one of the most common elements is gypsum wallboard, often known as drywall, used in the construction of walls and/or ceilings. One reason for the low cost of wallboard panels is that they are manufactured by a process that is fast and efficient. A slurry, including calcium sulfate hemihydrate and water, is used to form the core, and is continuously deposited on a paper cover sheet moving beneath a mixer. A second paper cover sheet is applied thereover and the resultant assembly is formed into the shape of a panel. Calcium sulfate hemihydrate reacts with a sufficient of the water to convert the hemihydrate into a matrix of interlocking calcium sulfate dihydrate crystals, causing it to set and to become firm. The continuous strip thus formed is conveyed on a belt until the calcined gypsum is set, and the strip is thereafter cut to form boards of desired length, which boards are conveyed through a drying kiln to remove excess moisture.

Walls and ceilings made from gypsum wallboard are conventionally constructed by affixing the panels to studs or joists and filling and coating the joints or seams between adjacent panels with a specially prepared adhesive called a joint compound. This process generally proceeds by placing a taping grade joint compound within the joint formed by the abutted edges of the wallboards and embedding a liquid-permeable tape within the taping compound. When dry (or set), a second coating including a topping grade joint compound is applied over the joint. This may be sanded lightly, then a third coat applied and conventionally finished. Another grade of joint compound is an all-purpose grade that may be used both for embedding the tape and for applying the finish coats.

There are two types of joint compounds that are commonly used. Compounds of the drying type become hard when the water evaporates. Setting type joint compounds become solid upon the absorption of water. Ready-mix formulations of setting type joint compounds often contain retarders to prevent the absorption of water during the shelf life of the product. When it is desirous to use the joint compound, it then becomes necessary to add an accelerator in order to overcome the effects of the retarder.

Drywall joint compounds may be sold either as a dry powder to be mixed with water, or in the form of a ready-mix compound. There are advantages to the ready-mix formula where it is inconvenient to provide or measure the water to be added at the job site. Ready mixed joint compound is typically supplied to the customer in either cardboard cartons or plastic pails in units having volumes of 3.5 to 4.5 gallons (13.25-17.03 L). An example of ready mix joint compound is U.S. Pat. No. 8,822,566, incorporated by reference.

Joint compound is supplied at a viscosity typically higher than what is applied at the jobsite. This allows the contractor to mix in additional water using a power drill and mixing paddle to achieve the desired application viscosity. Additives are used in all types of joint compounds to modify physical and chemical properties of the compound to suit particular purposes.

When customers encounter a problem with a building product of this type, they typically contact a manufacturer of that product to report the defect. If the wallboard or joint compound is applied by a contractor, as is often the case, the homeowner may not know what brand of building material has been used. Even if the homeowner does the work himself, he does not always save the label, container or other product identification. In these cases, it is not unusual for the homeowner to consult with or complain to a manufacturer with whom they are familiar, without being certain that the manufacturer actually made the gypsum-based building material installed in the owner's home.

The manufacturer then spends a significant amount of time investigating the source of the product about which they received a complaint. Often, they find that the product is that of another manufacturer and that the time spent on the investigation was wasted. Manufacturers of such products have a need for a way of quickly and easily determining whether they actually made the joint compound that has been called into question.

Besides gypsum wallboard panels and joint compound, a number of other compositions are used in building construction or remodeling products. These include, but are not limited to, plaster, textures, poured flooring, acoustical products and fiberboard. Any of these compositions are susceptible to questions of identification if a homeowner is unsatisfied with the product performance.

Commonly-assigned U.S. Pat. No. 8,642,346 discloses a tagging material for the above-identified building products. However, in order to determine if the tagging material is present, the sample of building material must be sent to a laboratory for analysis. Such analysis consumes significant time between when the sample is taken and when the results are received, identifying the source of the product being analyzed.

SUMMARY

At least one of these or other problems is reduced using a building material that is uniquely identifiable. An improved joint compound is disclosed into which is incorporated a marker or a tagging material that is easily identified in the field with a simple test. In the preferred embodiment, the present tagging material is identifiable using a conventional UV blacklight. Thus, using the present tagging material incorporated into the building material, such as joint compound, the source of the material is readily ascertainable in the field using a conventional hand-held UV blacklight. Also, the preferred tagging material is an optical brightener, similar to the compositions used in laundry detergents to brighten clothes. Another feature of the present composition is that the tagging material is effective in extremely small doses, in the range of 0.006%-0.003% weight percent of the building product composition, excluding water. Tests have shown that the addition of the preferred tagging material has not adversely affected the performance of the building product, and sufficient amounts of tagging material can be added without appreciably increasing the cost of production of the building product.

More specifically, a method of making an identifiable gypsum-based building product, includes incorporating a suitable amount of an optically identifiable tagging material into the product to be sensed by a conventional detecting device; applying the product with the tagging material in a conventional manner in the course of building construction, creating a finished building product; and analyzing the finished building product and optically detecting the presence of the tagging material in real time onsite.

In another embodiment, a building product with an identifiable tagging material that is identifiable onsite upon application using a UV blacklight, is provided and includes at least one filler, at least one binder, at least one thickener, water and a tagging material comprising between 0.003 and 0.006% by weight of the composition excluding water.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
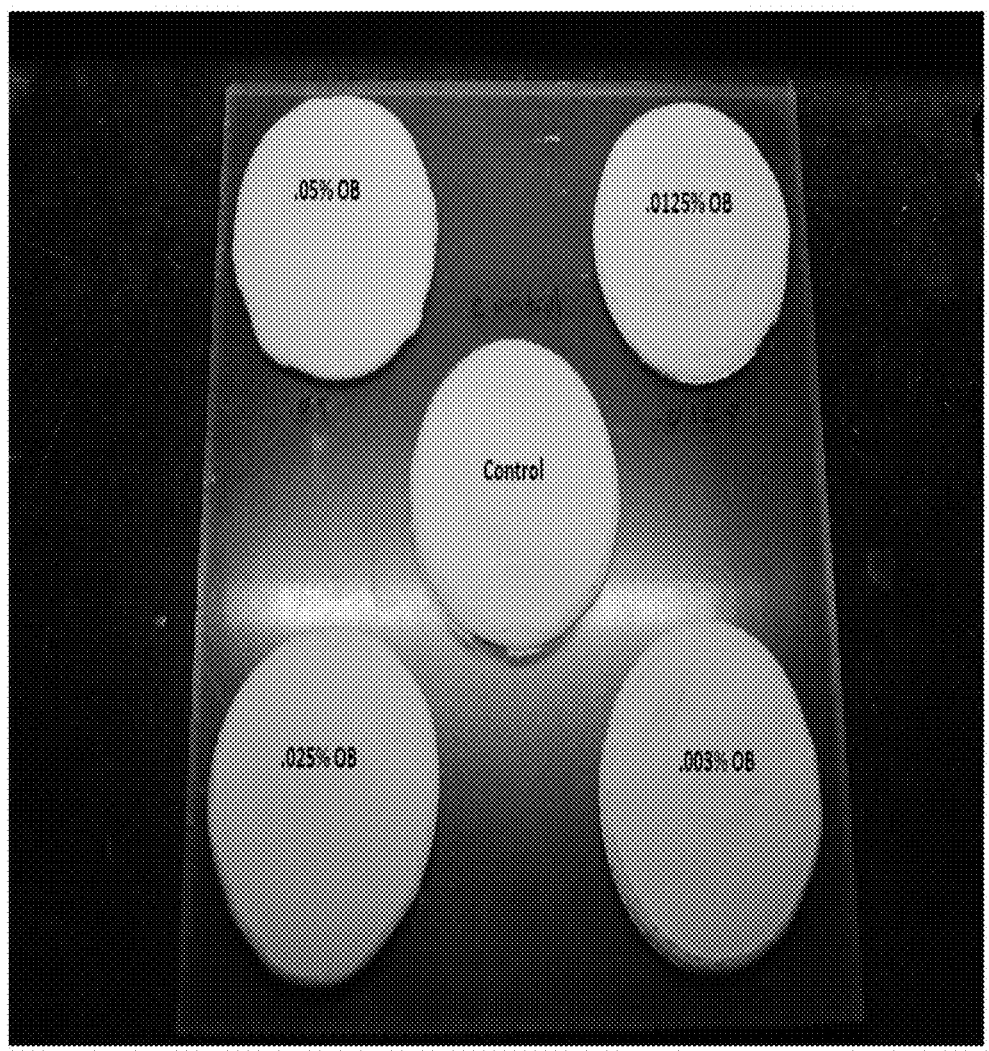
FIG. 1 is a photograph of a test scenario of five samples of joint compound containing various amounts of tagging material, and a control.

Where there is a possibility of having to identify a joint compound as originating with a particular manufacturer, it is advantageous to use a tagged joint compound. It is to be understood that the compositions and techniques described below are applicable in addition to joint compound, to any gypsum-containing building material, including wallboard panels, plasters, texturing products, acoustical products, poured floorings and the like. The present composition and techniques also apply to building materials having no gypsum. An example of a non-gypsum building material is a drying-type joint compound. Additional examples of building materials are those that include calcium carbonate, cement and polymeric binders, in combination with each other or with gypsum. In some embodiments, the building materials are normally used for the preparation and finishing of walls, ceilings and floors. In the discussion below, a joint compound is used as an exemplary building material, but it is contemplated that any building material may benefit from this technology.

As is well known in the art, preparation of the base joint compound, also referred to as the base compound, incorporates a filler, a binder, a thickener, preservatives, a non-leveling agent and water. Lightweight filler may be optionally included into the base compound to adjust the density of the composition. Filler for use in the base joint compound may be any of the calcium carbonate or calcium sulfate dihydrate fillers common to preparation of typical joint compounds and known to those skilled in the art. Fillers ground to median particle size between 5 and 40 microns are typically used. Usage levels are typically between 50% to 95% by weight of the total composition not including the water added (a dried component basis), although example of filler-free compounds do exist.

A latex emulsion binder is an important ingredient which is well known to those skilled in the joint compound art. Any of the conventional latex binders may be used, with polyvinyl acetate and ethylene vinyl acetate emulsions being preferred. If present, the latex binder ranges from about 0.5% to about 10% by weight of the composition prior to adding water, with some embodiments using 1% to about 8% (by weight on a dried component basis). The use of spray-dried binders is contemplated with usages ranging from 0.1% to 1.5% (by weight on a dried component basis).

It is generally preferred that the base joint compound include one or more thickeners. Conventional cellulosic thickeners, e.g. ethylhydroxy ethylcellulose, hydroxypropyl methylcellulose, methylhydroxypropyl cellulose, hydroxyethyl cellulose, methylhydroxyethyl cellulose and mixtures thereof, may be used in the present base joint compounds. The total amount of cellulosic thickener ranges from about 0.1% to about 3%, preferably 0.3 to 1% by weight of the total composition ingredients not including the water added. It is contemplated that other thickeners will be used instead of or in addition to the cellulosic thickener.

The present base joint compound optionally contains a non-leveling agent or suspending agent such as attapulgus or attapulgite clay. This ingredient provides non-leveling or anti-sag, slip, water retention, and water demand. In general, the amount of the non-leveling agent, if present, ranges from about 1% to about 10%, preferably 2% to 7% by weight of the base composition prior to adding water. Other clays such as sepiolite, bentonite and montmorillonite may also be used in the base joint compound, in addition to or instead of the clay. Non-clay non-leveling or suspending agents such as the types listed in U.S. Pat. No. 5,336,318, incorporated by reference, are of use in the present joint compound.

When preparing a ready-mix joint compound, it is preferable to provide for control of microbial growth in the wet medium during storage. One method of reducing microbes is by introducing a biocide that kills on contact. Examples of contact-kill biocides include household bleach (6% aqueous sodium hypochlorite) or chemicals for shock treatment of swimming pools, such as lithium or calcium hypochlorite. Although these additives will kill essentially all microbes present in the joint compound base at the time of manufacture, they will not prevent future microbial growth.

Conventional in-can preservatives, including MERGAL 174 liquid bactericide made by Troy Corporation, Florham Park, N.J. and/or NUOSEPT 91 liquid organic biocide are available from International Specialty Products, Wayne, N.J., are used for continuing suppression of microbial growth. They can be used in combination with or in place of the contact-kill treatments. Combinations of preservatives are also contemplated.

Water is added in amounts selected to produce a base joint compound of a desired viscosity. A vacuum step is performed after mixing to remove excess air from the mixture. Some embodiments of the invention typically target a viscosity of between 200-800 Brabender Units after vacuum using a pin type probe (Type A) and 250 cmg torque head using a Brabender Viscocorder.

If the joint compound is preferred to be a lightweight, ready-mixed joint compound, the lightweight or low density property can be provided by incorporating an expanded perlite into the base joint compound in accordance with the disclosure in U.S. Pat. No. 4,454,267, incorporated by reference. It is well known in the art that it is preferred that the expanded perlite should have a particle size which will pass through a 100 mesh screen if it is to be incorporated into a joint compound base. Also, the perlite is preferred to represent 8-10% by weight of the composition excluding water. In a ready-mixed joint compound, the expanded perlite is optionally treated to render it water-insensitive or left uncoated. If it is advantageous to treat the expanded perlite, there are several ways to render the expanded perlite water-insensitive, one of which is disclosed in U.S. Pat. No. 4,525,388, incorporated by reference. Another method is to treat the expanded perlite with a silicone or siloxane compound, but other materials may be used to render it water-insensitive (i.e., water-repellent). Specially treated expanded perlite is commercially available from suppliers such as Silbrico Corporation, Hodgkins, Ill.

Conventional ready-mixed joint compounds frequently contain mineral fillers, such as diatomaceous earth, mica, talc, or sericite to provide reduced cracking and shrinkage, and added slip. When used in the present base joint compound, the mica or talc may be between about 2% and about 15% by weight of the composition excluding water.

Additional ingredients frequently used in joint compounds are contemplated for use in the present joint compound system. These ingredients optionally include, but are not limited to humectants, fillers, wetting agents, kaolin, defoamers and plasticizers which are also useful in the joint compound base or in the additive blends.

Polyethylene oxide such as the POLYOX polyethylene oxide water-soluble resin product line from Dow Chemical Company, Midland, Mich., is a useful additive for increased viscosity and lubricity. Usage levels are typically 0.05 to 1% by weight of the composition excluding water. This additive is preferably applied as a discrete entity into the base joint compound.

Tagging or adding of a marker or tagging material to the joint compound occurs during product manufacture, when a tagged filler is added to a base joint compound composition. The present marker to tagging material may be used with any type of ready-mix joint compound that could benefit from addition of a premeasured additive at the time the joint compound is used. Both setting type and drying type joint compounds could be marked or tagged as described below.

Manufacture of the ready mixed joint compound includes combining of wet with dry components in a mixer. Some ingredients are available in either dry or liquid form. The preferred binder, a latex binder, is a liquid, but other binders are available as powders. All components, including the tagging material, are grouped as to their physical form. The wet components are generally blended directly in the mixer. Water is placed in the mixer and first blended with the other wet components, such as the surfactant additive and the binder, if they are in liquid form. The dry components generally include the fillers, suspending agents and thickeners. If provided as a powder, the binder is also mixed with the dry components. These components are blended together before addition to the mixer using any technique known in the art to blend dry ingredients together. Powder feeders are optionally used to disperse the suspending agents or thickeners in with the fillers as they are moved to the mixer by conveyor.

After the wet ingredients have been combined, the dry components are mixed in with the wet components in the mixer. Mixing continues until a homogeneous mixture is obtained. Additional water is added, if necessary, to achieve a desired viscosity. This viscosity will vary depending on exactly what type of joint compound is being prepared, but the target viscosity is generally between 350-850 Brabender units. Also, as described above, a vacuum is applied to the mixture to remove excess air.

Gypsum board products and their manufacture are described in U.S. Pat. Nos. 6,893,752, 5,320,677 and 7,413,603 are directed to the use and manufacture of fiberboard products. Gypsum-based flooring products are revealed in U.S. Pat. Nos. 7,056,964 and 7,504,165. Each of the previous five patents is incorporated by reference into this application in its entirety. The following examples demonstrate specific embodiments of this invention. They are not intended to define or limit the scope of the invention in any way.

Referring now to Table 1, the composition of a suitable joint compound is described, which generally incorporates the list of ingredients discussed above, and is well known in the art of joint compound manufacture. The main distinctive ingredient is Benetex® OB-M1 fluorescent Whitening Agent, also referred to as an optical brightener, produced by Mayzo, Inc., Suwanee, Ga. 30024. The preferred optical brightener is a derivative of distyryl biphenyl (DSBP) compound with a formula of $C_{28}H_{20}S_2O_6Na_2$. Other optical brighteners are well known in the art of laundry detergent formulation, and are also considered suitable for the present composition. It will be seen that in Table 1, the various tagged samples are identified by the weight percentage of the optical brightener. The control (no brightener) is compared against the amounts of the tagged joint compound: 0.05%; 0.025%; 0.0125%; 0.006%; and 0.003% all by weight of the composition, excluding water.

The tagged samples were mixed using the following procedure, which was intended to simulate actual factory production procedures in a laboratory setting:

1. Weigh raw materials in the order listed on Table 1, strike through gram amount once the item is added to the vessel.
2. Check the amount weighed to the theoretical weight for each ingredient.
3. Secure the lid on a pail containing the raw materials and shake for approximately 30 seconds to dry blend the ingredients.
4. To the Hobart mixing bowl, weigh the initial water, latex and preservative. If other liquid ingredients are used, add to the bowl by weight.
5. Add the powders to the Hobart mixing bowl and mix by hand until the powders are wetted.
6. Add the wetted mixture in the bowl to the Hobart mixer, lock in place, and mix on setting #1 for 1.5 minutes.
7. After the initial mix is complete, stop the mixer and clean the paddle using a metal spatula, putting the material from the spatula back into the mixture.
8. Wipe the bowl sides and bottom clean with a rubber spatula and place the mixture back on the Hobart mixer. Add the remaining water and mix an additional 1.5 minutes.
9. Stop the Hobart mixer and fill a ½ pint cup to record the viscosity.

If the desired viscosity is achieved, transfer the material from the ½ pint container to the mixture and place the bowl in the vacuum mixer set to a desired vacuum setpoint (15" or 27"). Close the lid and set the timers to 3 minutes. Once the vacuum has shut off and released the air, open the lid and remove the bowl. Fill a ½ pint container and record the viscosity. Transfer all of the compound into a stainless steel pot or bowl. Seal the edge with masking tape and a Plexiglas cover. Set aside for 24 hours.

If the desired viscosity is NOT achieved, add trim water, mix 1.5 minutes. Continue to add trim water until the desired viscosity is reached. Once the desired viscosity is achieved, transfer the material from the ½ pint container to the mixture in the bowl. Place the bowl in the vacuum mixer set to a desired vacuum set point (15" or 27"). Close the lid and set the timer to 3 minutes. Once the vacuum pump has shot off, and the air is released, open the lid and remove the bowl. Fill a ½ pint container and record the viscosity. Transfer all of the compound into a stainless steel pot or bowl. Seal the edge with masking tape and a Plexiglas cover. Set the bowl aside for 24 hours. It will be understood that from this procedure, the optical brightener is uniformly distributed throughout the building product, here a joint compound.

TABLE 1A

| M# | RAW MATERIALS | Control | | 0.05% Additive | |
|---|---|---|---|---|---|
| 70283 | Omyacarb BP (Calcium Carbonate) | 81.36% | 813.64 | 81.31% | 813.14 |
| 72120 | Grefco HP 2000 (Perlite) | 9.56% | 95.59 | 9.56% | 95.59 |
| 65581 | Min-U-Gel FG (Attapulgite Clay) | 4.55% | 45.52 | 4.55% | 45.52 |
| 79853 | Cellosize DCS HV (Thickener) | 0.63% | 6.26 | 0.63% | 6.26 |
| 72011 | Mecellose PMH-9860 (Thickener) | 0.32% | 3.22 | 0.32% | 3.22 |
| 64949 | Celvol 205-S (Polyvinyl Alcohol) | 0.28% | 2.84 | 0.28% | 2.84 |
| — | Benetex OB M1 (Optical Brightener) | | | 0.05% | 0.50 |
| | dry weight (grams) | | 967.07 | | 967.07 |
| 81608 | Encor 133 (Latex) | 2.85% | 47.42 | 2.85% | 47.42 |
| 66685 | Mergal 174 II (Preservative) | 0.30% | 2.96 | 0.30% | 2.96 |
| 12594 | bleach (Disinfectant) | 0.15% | 1.52 | 0.15% | 1.52 |
| | Percent non-volatile/total weight | 100.00% | 1018.97 | 100.00% | 1018.97 |
| | Initial H2O (mL) | | 850 | | 850 |
| | Viscosity (BU) | | 193 | | 180 |
| | Initial Density (lb/gal) | | 9.05 | | 9.57 |
| | Viscosity after Vac (BU) | | 214 | | 202 |
| | Vacuumed Density (lb/gal) | | 8.80 | | 9.16 |
| | 24 Hr. Viscosity (BU) | | 285 | | 280 |
| | 24 Hr. Density (lb/gal) | | 11.15 | | 11.33 |
| | pH | | 9.00 | | 8.80 |

TABLE 1B

| RM# | RAW MATERIALS | 0.025% Additive | | 0.0125% Additive | |
|---|---|---|---|---|---|
| 70283 | Omyacarb BP (Calcium Carbonate) | 81.34% | 813.39 | 81.35% | 813.51 |
| 72120 | Grefco HP 2000 (Perlite) | 9.56% | 95.59 | 9.56% | 95.59 |
| 65581 | Min-U-Gel FG (Attapulgite Clay) | 4.55% | 45.52 | 4.55% | 45.52 |
| 79853 | Cellosize DCS HV (Thickener) | 0.63% | 6.26 | 0.63% | 6.26 |
| 72011 | Mecellose PMH-9860 (Thickener) | 0.32% | 3.22 | 0.32% | 3.22 |
| 64949 | Celvol 205-S (Polyvinyl Alcohol) | 0.28% | 2.84 | 0.28% | 2.84 |
| — | Benetex OB M1 (Optical Brightener) | 0.025% | 0.25 | 0.0125% | 0.13 |
| | dry weight (grams) | | 967.07 | | 967.07 |
| 81608 | Encor 133 (Latex) | 2.85% | 47.42 | 2.85% | 47.42 |
| 66685 | Mergal 174 II (Preservative) | 0.30% | 2.96 | 0.30% | 2.96 |
| 12594 | bleach (Disinfectant) | 0.15% | 1.52 | 0.15% | 1.52 |
| | Percent non-volatile/total weight | 100.00% | 1018.97 | 100.00% | 1018.96 |
| | Initial H2O (mL) | | 850 | | 850 |
| | Viscosity (BU) | | 182 | | 172 |
| | Initial Density (lb/gal) | | 9.40 | | 9.12 |
| | Viscosity after Vac (BU) | | 208 | | 203 |
| | Vacuumed Density (lb/gal) | | 9.21 | | 8.91 |
| | 24 Hr. Viscosity (BU) | | 283 | | 276 |
| | 24 Hr. Density (lb/gal) | | 11.21 | | 10.96 |
| | pH | | 9.05 | | 8.95 |

TABLE 1C

| RM# | RAW MATERIALS | 0.006% Additive | | 0.003% Additive | |
|---|---|---|---|---|---|
| 70283 | Omyacarb BP (Calcium Carbonate) | 81.36% | 813.58 | 81.36% | 813.61 |
| 72120 | Grefco HP 2000 (Perlite) | 9.56% | 95.59 | 9.56% | 95.59 |
| 65581 | Min-U-Gel FG (Attapulgite Clay) | 4.55% | 45.52 | 4.55% | 45.52 |
| 79853 | Cellosize DCS HV (Thickener) | 0.63% | 6.26 | 0.63% | 6.26 |
| 72011 | Mecellose PMH-9860 (Thickener) | 0.32% | 3.22 | 0.32% | 3.22 |

TABLE 1C-continued

| RM# | RAW MATERIALS | 0.006% Additive | | 0.003% Additive | |
|---|---|---|---|---|---|
| 64949 | Celvol 205-S (Polyvinyl Alcohol) | 0.28% | 2.84 | 0.28% | 2.84 |
| — | Benetex OB Ml (Optical Brightener) | 0.006% | 0.06 | 0.003% | 0.03 |
| | dry weight (grams) | | 967.07 | | 967.07 |
| 81608 | Encor 133 (Latex) | 2.85% | 47.42 | 2.85% | 47.42 |
| 66685 | Mergal 174 II (Preservative) | 0.30% | 2.96 | 0.30% | 2.96 |
| 12594 | bleach (Disinfectant) | 0.15% | 1.52 | 0.15% | 1.52 |
| | Percent non-volatile/total weight | 100.00% | 1018.97 | 100.00% | 1018.97 |
| | Initial H2O (mL) | | 850 | | 850 |
| | Viscosity (BU) | | 185 | | 185 |
| | Initial Density (lb/gal) | | 9.20 | | 9.21 |
| | Viscosity after Vac (BU) | | 210 | | 213 |
| | Vacuumed Density (lb/gal) | | 8.92 | | 8.98 |
| | 24 Hr. Viscosity (BU) | | 284 | | 283 |
| | 24 Hr. Density (lb/gal) | | 11.08 | | 11.14 |
| | pH | | 8.90 | | 8.93 |

From Tables 1A-1C, it is seen that the addition of the optical brightener did not significantly alter the properties of the joint compound, comparing the tagged samples to the control. Among the properties evaluated were pH, viscosity, and weight/gallon. Referring now to Tables 2-6, a comparison of the tagged samples to the control reveals that the properties and performance characteristics of the tagged joint compound remained equivalent to those of the control. Among the parameters evaluated were, cracking (Table 2), smoothness of finish (Table 2), bond to paper (Table 3), measured shrinkage (Table 4), paint adhesion (Tables 5A-5C) and cost per container of adding the optical brightener (Table 6). At the lowest concentration (0.003% wt. excluding water), the cost of adding the brightener to the container was 1 cent. In addition to the listed parameters, the density of the resulting joint compound was also evaluated and the tagged samples were found to have comparable density to the control. The density of a joint compound refers to the operational feel of the material when a user manipulates or trowels it in a wallboard panel joint.

TABLE 2

Cracking of joint compound over deep fill

| Deep cracks | 0" | 0" | 0" | 0" | 0" | 0" |
|---|---|---|---|---|---|---|
| Shallow cracks | 2" | 0" | 0" | 0" | 0" | 2" |
| Smoothness of finish | coarse | very smooth | smooth | moderately smooth | moderate | moderately coarse |

TABLE 3

Bond to Paper Tape: Scale rating from 0-7 (0 equals no fiber tear) (7 equals 100% fiber tear)

| Bond at 75°/50% RH | 7 | 7 | 7 | 7 | 7 | 7 |
|---|---|---|---|---|---|---|

TABLE 4

% Shrinkage - non ASTM method

| measured shrinkage | 24.60% | 27.10% | 26.10% | 25.10% | 24.60% | 24.60% |
|---|---|---|---|---|---|---|

TABLE 5A

| | Control | | 0.05% Additive | |
|---|---|---|---|---|
| Paint Adhesion | Not Primed | Primed | Not Primed | Primed |
| 3M for production painting #2020 | 100% | 100% | 100% | 100% |
| 3M hard to stick surfaces #2060 | 100% | 100% | 100% | 100% |
| 3M Scotch Blue #2080 | 100% | 100% | 100% | 100% |
| 3M Scotch Blue #2090 | 100% | 100% | 100% | 100% |

TABLE 5B

| | 0.025% Additive | | 0.0125% Additive | |
|---|---|---|---|---|
| Paint Adhesion | Not Primed | Primed | Not Primed | Primed |
| 3M for production painting #2020 | 100% | 100% | 100% | 100% |
| 3M hard to stick surfaces #2060 | 100% | 100% | 100% | 100% |
| 3M Scotch Blue #2080 | 100% | 100% | 100% | 100% |
| 3M Scotch Blue #2090 | 100% | 100% | 100% | 100% |

TABLE 5C

| | 0.006% Additive | | 0.003% Additive | |
|---|---|---|---|---|
| Paint Adhesion | Not Primed | Primed | Not Primed | Primed |
| 3M for production painting #2020 | 100% | 100% | 100% | 100% |
| 3M hard to stick surfaces #2060 | 100% | 100% | 100% | 100% |
| 3M Scotch Blue #2080 | 100% | 100% | 100% | 100% |
| 3M Scotch Blue #2090 | 100% | 100% | 100% | 100% |

TABLE 6

| Cost Impact of adding OB M1 to the batch | | | | | | |
|---|---|---|---|---|---|---|
| Cost per Container | $2.30 | $2.45 | $2.37 | $2.33 | $2.32 | $2.31 |

Figure 2:
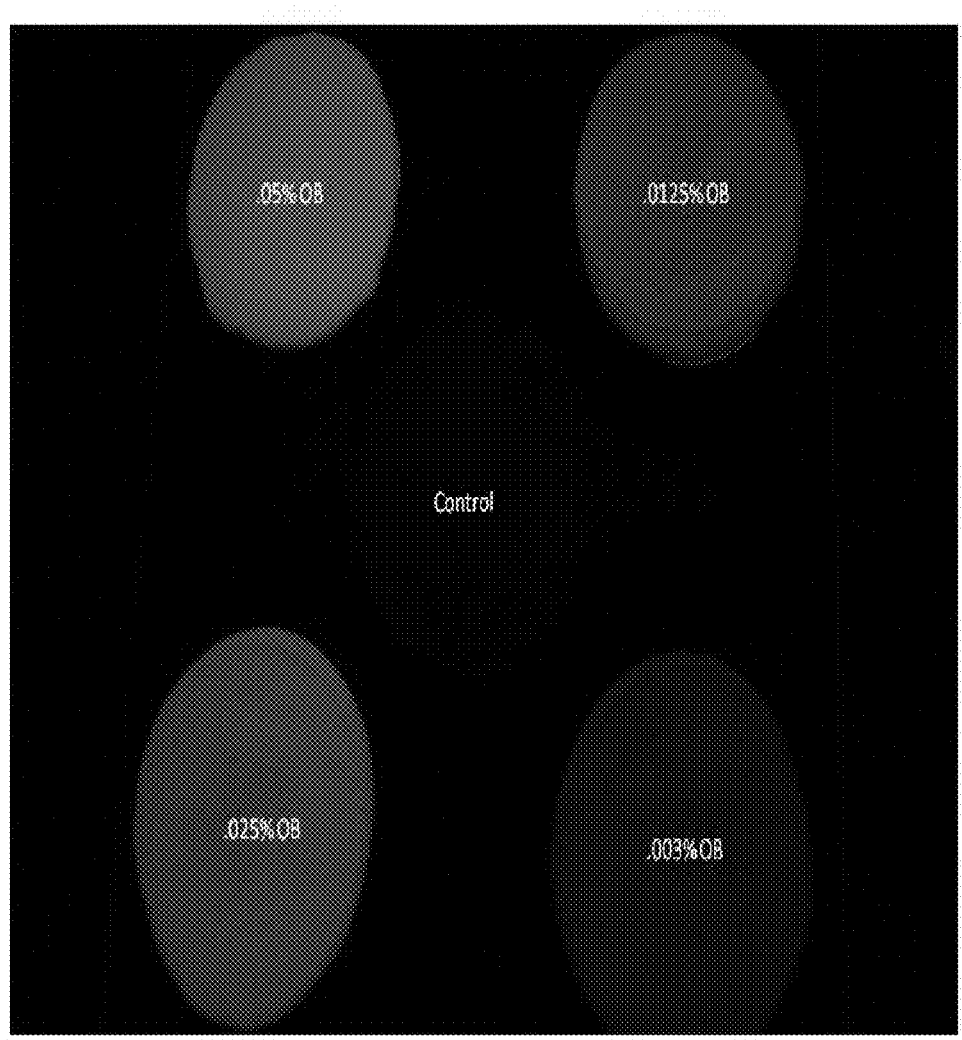
FIG. 2 is a color image of the results of the test of FIG. 1 illuminated by a UV blacklight.

Referring now to FIGS. 1 and 2, the samples listed in Table 1 are placed on a tray in FIG. 1, then placed in a dark room and illuminated with a conventional UV blacklight. Such blacklights are inexpensive and are readily available from a variety of retail stores, and include flashlight and other hand-held embodiments. While the control was not visible under the blacklight, each of the tagged samples was visible. Also, it is seen that the optical brightener is uniformly visible across the entire sample. Predictably, the 0.05% sample was the brightest, and the 0.003% sample was the least bright of the group, but was still visible under the blacklight by the naked eye. As such, even the 0.003% sample is considered suitable for use in field identification and verification using a hand-held blacklight to verify the source of the building material.

Referring now to Table 7, the relative brightness of the control and the tagged samples from 0.05 to 0.003% wt. (except for 0.006%) were analyzed using Image J software, a public domain Java image processing program developed by the National Institutes of Health (NIH) Image (http://imagej.nih.gov/ij/). Four examples of each of the control and the tested tagged percentage samples from Table 1 were evaluated as to their fluorescent brightness. The Image J software measured both density and Greyscale for each sample. In the far right column of Table 7, CTCF refers to Corrected Total Cell Fluorescence which is a brightness index obtained by taking the Integrated Density, subtracting the area and multiplying by the Mean. CTCF accounts and adjusts for the halo effect around the perimeter of an object, and removes that from the fluorescent brightness evaluation.

The resulting CTCF values reflect that even the sample with the lowest amount of optical brightener, at 0.003%, had a CTCF value of 624,898, which is more than 10 times the corresponding value of the control at 50,762, representing a 10 times brighter sample with lowest level of optical brightener. As expected, the remaining samples of 0.0125%, 0.025% and 0.5% were increasingly bright as the amount of optical brightener increased. The 0.5% sample with the most optical brightener had a significantly greater CTCF value of 2,289,072, or 45 times greater than the CTCF value of the control.

TABLE 7

| | Area | Mean | Min Grey | Max Grey | Int Den | CTCF |
|---|---|---|---|---|---|---|
| Control | 21002 | 3.755 | 1 | 13 | 78868 | 50762 |
| Control BG 1 | 240 | 1.612 | 1 | 2 | 387 | |
| Control BG 2 | 240 | 1.008 | 1 | 2 | 242 | |
| Control BG 3 | 240 | 1.733 | 1 | 2 | 416 | |
| Control BG 4 | 240 | 1.000 | 0 | 2 | 240 | |
| BG Average | 240 | 1.33825 | 0.75 | 2 | 321.25 | |
| .003% OB | 21002 | 30.628 | 23 | 39 | 643254 | 624898 |
| .003% OB-BG 1 | 240 | 0.942 | 0 | 2 | 226 | |
| .003% OB-BG 2 | 240 | 0.929 | 0 | 1 | 223 | |
| .003% OB-BG 3 | 240 | 0.758 | 0 | 2 | 182 | |
| .003% OB-BG 4 | 240 | 0.867 | 0 | 2 | 208 | |
| BG Average | 240 | 0.874 | 0 | 1.75 | 209.75 | |
| .0125% OB | 21002 | 73.279 | 59 | 87 | 1539011 | 1513415 |
| .0125% OB-BG 1 | 240 | 0.888 | 0 | 1 | 213 | |
| .0125% OB-BG 2 | 240 | 1.329 | 0 | 2 | 319 | |
| .0125% OB-BG 3 | 240 | 1.696 | 0 | 5 | 407 | |
| .0125% OB-BG 4 | 240 | 0.962 | 0 | 2 | 231 | |
| BG Average | 240 | 1.21875 | 0 | 2.5 | 292.5 | |
| .025% OB | 21002 | 89.391 | 68 | 99 | 1877390 | 1855642 |
| .025% OB-BG 1 | 240 | 1.092 | 0 | 3 | 262 | |
| .025% OB-BG 2 | 240 | 0.996 | 0 | 1 | 239 | |
| .025% OB-BG 3 | 240 | 1.012 | 0 | 2 | 243 | |
| .025% OB-BG 4 | 240 | 1.042 | 0 | 2 | 250 | |
| BG Average | 240 | 1.0355 | 0 | 2 | 248.5 | |
| .05% OB | 21002 | 110.215 | 91 | 119 | 2314731 | 2289072 |
| .05% OB-BG 1 | 240 | 1.338 | 1 | 3 | 321 | |
| .05% OB-BG 2 | 240 | 0.929 | 0 | 4 | 223 | |
| .05% OB-BG 3 | 240 | 1.608 | 1 | 3 | 386 | |
| .05% OB-BG 4 | 240 | 1.012 | 1 | 2 | 243 | |
| BG Average | 240 | 1.22175 | 0.75 | 3 | 293.25 | |

Figure 3:
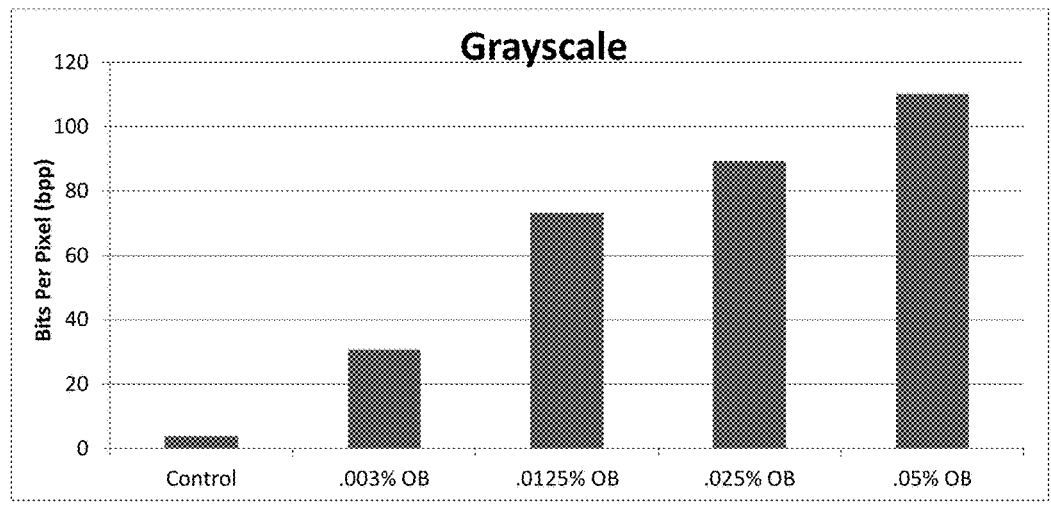
FIG. 3 is a graph of Grayscale vs. Bitts per pixel of the various samples of FIG. 1.
Figure 4:
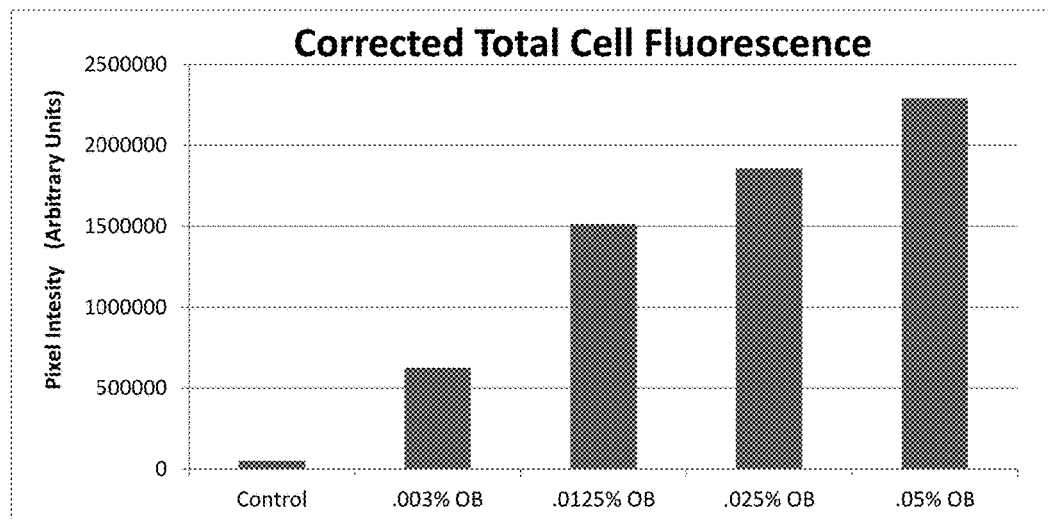
FIG. 4 is a graph of Corrected Total Cell Fluorescence vs Pixel Intensity for the samples of FIG. 1.
Figure 5:
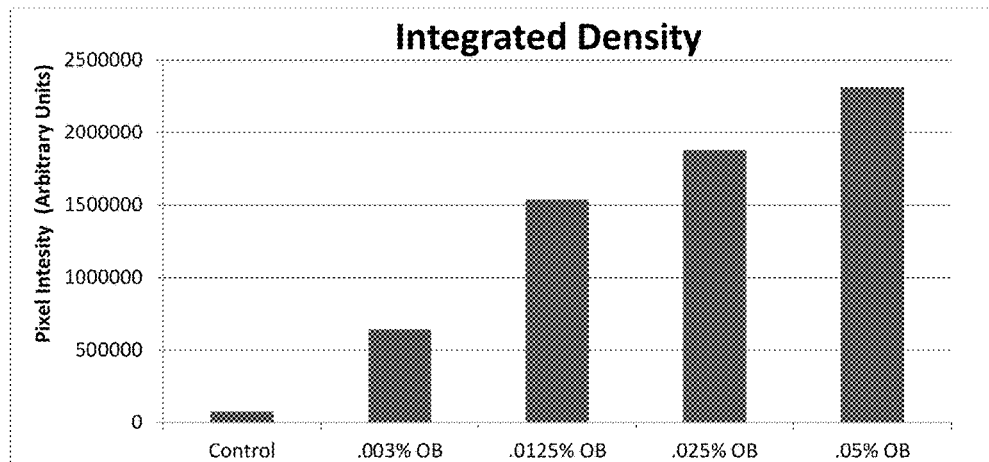
FIG. 5 is a graph of Integrated Density vs. Pixel Intensity for the samples of FIG. 1.
Figure 6:
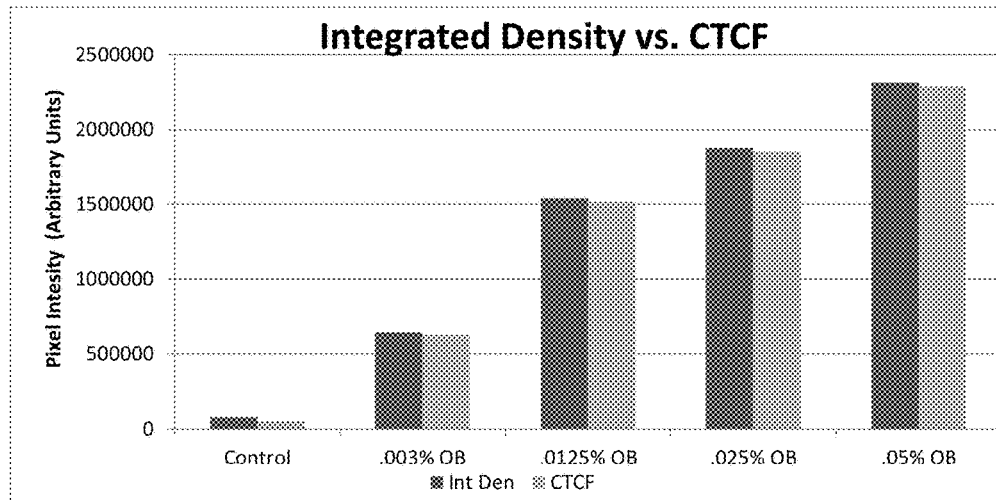
FIG. 6 is a graph of Integrated Density/CTCF vs. Pixel Intensity for the samples of FIG. 1.

Referring now to FIGS. 3-6, a series of representations of the data of Table 7 are presented, to graphically illustrate the differences in brightness of the various tested samples. FIG. 3 depicts the various levels of brightness in terms of fluorescence from the optical brightener added to ready mix joint compound prepared as described above. The data displays the mean greyscale in bits per pixel (bpp). The minimum bpp is 0, which is black, and the maximum is 250, which is white. FIG. 4 is a plot of Corrected Total Cell Fluorescence (CTCF) by pixel intensity. Again, the smallest amount of optical brightener, 0.003% has a pixel intensity that is 500,000 greater than the control, and the greatest amount of optical brightener, 0.5%, has a pixel intensity that is 2,500,000 greater than the control. FIG. 5 depicts Integrated Density, or the pixel depth of an image, which can be used to compare various brightness levels in an image. Integrated Density is used to calculate Corrected Total Cell Fluorescence, as described above. As seen in FIG. 4, the smallest amount of optical brightener, 0.003% is significantly brighter than the control, and that difference increases in proportion with the amount of optical brightener added. FIG. 6 reflects the difference between Integrated Density and CTCF. In this case, the 0.006$ % sample was included, and the 0.05% sample was excluded. Also, the control has a negative CTCF because the samples in FIG. 1 were applied over a gypsum wallboard panel, which has face paper that emits a fluorescence, presumably from the paper manufacturing process, even though the control sample did not emit any fluorescence. As was the case in FIGS. 3-5, the samples with even a small amount of optical brightener were significantly brighter than the control.

Thus, it is evident that a building product, such as the present joint compound, can be equipped with very small amounts of a tagging material, such as optical brightener, in the range of 0.003 to 0.006% by weight of the composition excluding water, and can still be identifiable in the field in real time, onsite, using a conventional UV blacklight. By using the present product, manufacturers can now more readily and accurately identify their products to address product complaints.

While a particular embodiment of the present fluorescent building product and related detection method has been described herein, it will be appreciated by those skilled in the art that changes and modifications may be made thereto without departing from the invention in its broader aspects and as set forth in the following claims.

The invention claimed is:

1. A method of making and analyzing a finished building structure comprising an identifiable gypsum-based wallboard panel, the method comprising:
    incorporating an optically identifiable tagging material into the wallboard panel containing gypsum, wherein said tagging material is provided in concentration in a range of 0.003% to 0.006% by weight of the wallboard panel, excluding water;
    using the wallboard panel to construct a finished building structure at a location;
    analyzing the finished building structure at the location by illuminating the finished building structure with only a handheld detecting device; and
    optically detecting the presence of the tagging material with the handheld detecting device in real time at the location of the finished building structure by observing whether the tagging material is visible under illumination provided by the handheld detecting device.

2. The method of claim 1, wherein said tagging material is an optical brightener and is uniformly distributed in the wallboard panel.

3. The method of claim 1, wherein upon employment of the detecting device, the tagging material is visible across the entire wallboard panel.

4. The method of claim 1, wherein the detecting device is a hand-held UV blacklight.

5. The method of claim 4, wherein upon exposure to the UV blacklight, the wallboard panel with said tagging material has a pixel intensity that is at least 500,000 greater than a control product without the tagging material.

6. The method of claim 4, wherein, upon exposure to the UV blacklight, the wallboard panel with said tagging material is at least ten times brighter than a control product without the tagging material.

7. A wallboard panel comprising:
    a gypsum;
    at least one filler;
    at least one binder;
    at least one thickener;
    water; and
    a tagging material comprising between 0.003 and 0.006% by weight of the wallboard panel excluding water,
    wherein the tagging material is identifiable in real time at a location where the wallboard panel is installed using illumination with a handheld UV blacklight only.

8. The wallboard panel of claim 7, wherein the tagging material is an optical brightener identifiable using the UV blacklight.

9. The wallboard panel of claim 7, wherein the tagging material has the formula $C_{28}H_{20}S_2O_6Na_2$.

* * * * *